United States Patent
Maeda et al.

(10) Patent No.: US 6,554,766 B2
(45) Date of Patent: Apr. 29, 2003

(54) ENDOSCOPE DEVICE

(75) Inventors: Toshinari Maeda, Hachioji (JP); Hitoshi Mizuno, Koganei (JP); Yuta Okada, Hachioji (JP); Eiichi Kobayashi, Tama (JP); Toshimasa Kawai, Yokohama (JP); Yuichi Ikeda, Tama (JP)

(73) Assignee: Olympus Optical Co., Ltd., Tokyo (JP)

( * ) Notice: Subject to any disclaimer, the term of this patent is extended or adjusted under 35 U.S.C. 154(b) by 6 days.

(21) Appl. No.: 09/860,713

(22) Filed: May 18, 2001

(65) Prior Publication Data

US 2002/0103418 A1 Aug. 1, 2002

(30) Foreign Application Priority Data

Jan. 30, 2001 (JP) .......................................... 2001-022203

(51) Int. Cl.[7] ................................................ A61B 1/00
(52) U.S. Cl. ...................................... 600/132; 600/146
(58) Field of Search ................................ 600/102, 114, 600/117, 132, 118, 112, 139, 146, 147

(56) References Cited

U.S. PATENT DOCUMENTS

| | | | | |
|---|---|---|---|---|
| 4,559,928 A | * | 12/1985 | Takayama | 388/838 |
| 4,721,099 A | * | 1/1988 | Chikama | 138/118 |
| 4,854,301 A | * | 8/1989 | Nakajima | 297/217.3 |
| 5,441,042 A | * | 8/1995 | Putman | 600/102 |
| 5,524,180 A | * | 6/1996 | Wang et al. | 600/117 |
| 5,779,623 A | * | 7/1998 | Bonnell | 414/431 |
| 6,236,876 B1 | * | 5/2001 | Gruner et al. | 600/114 |

* cited by examiner

Primary Examiner—Teresa Walberg
Assistant Examiner—Thor Campbell
(74) Attorney, Agent, or Firm—Scully, Scott, Murphy & Presser

(57) ABSTRACT

An endoscope device includes an inserting portion having a curving portion, electric motors for generating driving forces for curving the curving portion, an operation unit for controlling the drive of the electric motors, a universal cord the base end of which is connected to an endoscope external unit, a coupling member with which the respective one ends of the inserting portion and the universal cord are coupled and which has a treatment tool inserting port, a holding unit for holding the coupling member, and a holding member for disposing the holding unit at a predetermined position of an operation bed. According to this arrangement, the operability of a surgeon can be improved by improving not only a curving operability but also the insertion operability of an inserting portion and the operability of a treatment tool.

13 Claims, 16 Drawing Sheets

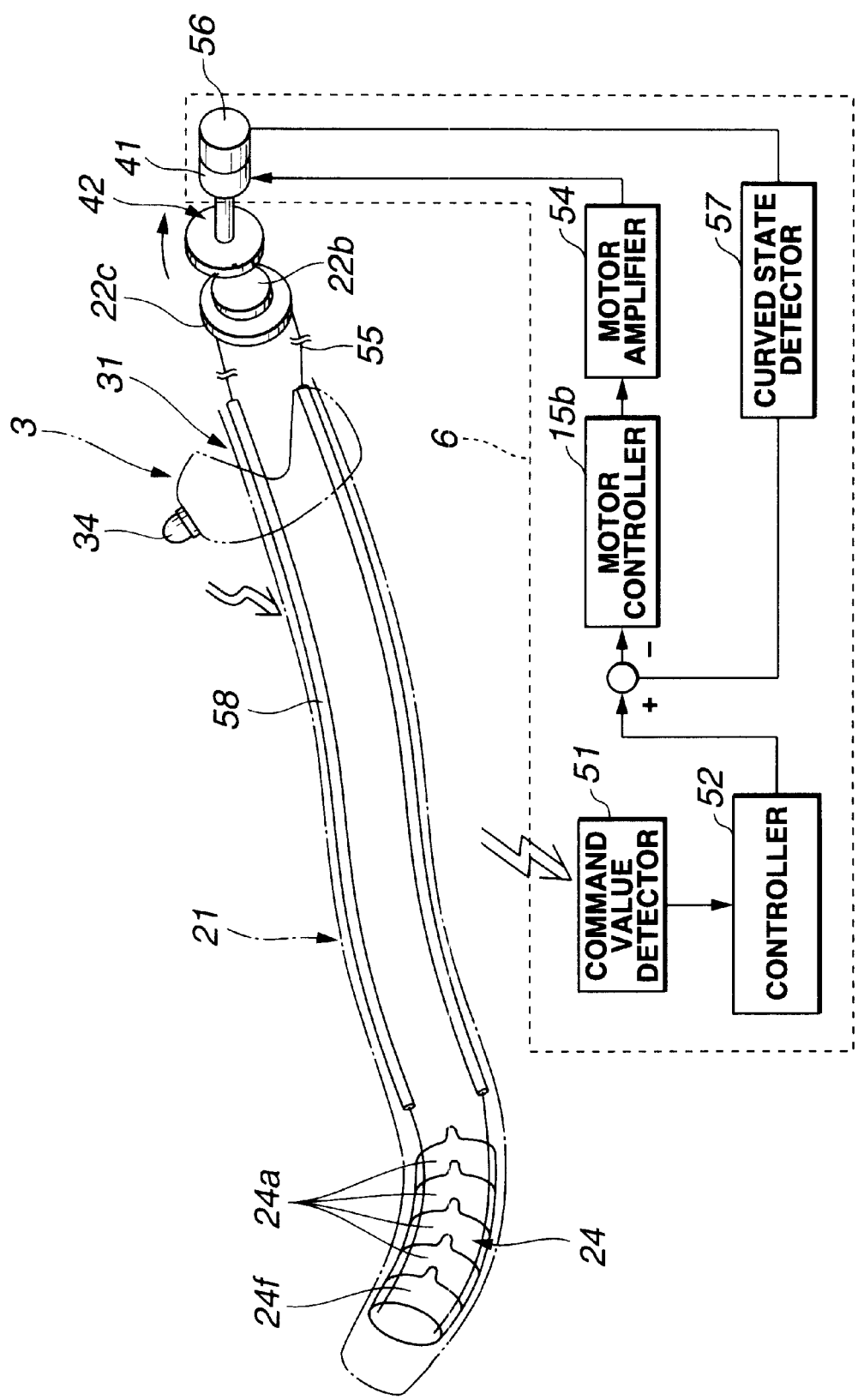

ENDOSCOPE DEVICE

This application claims benefits of Japanese Application No. 2001-22203 filed in Japan on Jan. 30, 2001, the contents of which are incorporated by this reference.

FIELD OF INVENTION

The present invention relates to an endoscope device, and more particularly, to an endoscope device for curving and driving a curving portion disposed to an inserting portion by the driving force of an electric motor.

DESCRIPTION OF RELATED ARTS

Recently, there have been widely used medical endoscope devices capable of observing intracavital diseased parts by inserting a slender inserting portion into a body cavity and executing various medical treatments when necessary using a treatment tool inserted into a treatment tool channel. Further, industrial endoscope devices capable of making observation and the like of the interiors of boilers, engines, and the like have been widely used also in industrial fields.

For example, in the above medical endoscope devices, a curving portion, which can curve, for example, up, down, left, right, and the like, is disposed to the extreme end side of an inserting portion in order to improve an inserting property when the medical endoscope devices are inserted into a bending portion such as an intestine and the like and to permit an observation optical system disposed at the extreme end thereof to be directed in a desired direction.

When the curving portion is to be curved in a desired direction, a surgeon generally executes a curving operation by pulling and loosening a curving wire coupled with a curving knob, which is disposed to an operation unit, and with the curving portion by manually operating the curving knob.

However, in the fields where inspection is carried out using endoscopes, there has been the need for an endoscope in which equipment can reliably be operated as simply as possible with a less number of operations so that a surgeon can concentrate on inspection and that the reliability of the inspection can be improved. Thus, endoscopes, which require a surgeon not only to grip them with his or her hands and fingers but also to operate a curving knob and various kinds of operation switches with a plurality of fingers, have a problem that they have complexity from a viewpoint of simplicity of operation.

To solve this problem, there has been disclosed the arrangement of a plurality of endoscopes that include electric motors in the operation unit thereof and are provided with an electrically operated angle controller which permits a surgeon to curve a curving portion by operating a joystick acting as a curve control mechanism with a single finger.

Further, in order to overcome a newly occurred disadvantage that operability is made bad by an increase in size and weight of an operation unit main body when the electric motor is included in the operation unit, there also has been disclosed the arrangement of a plurality of endoscope devices which have electric motors, which are disposed on the side of an endoscope external unit, and an electrically operated angle controller. The angle controller is provided with a driving force transmission unit, to which the driving forces of the electric motors are transmitted, and is disposed in the vicinity of a connector disposed to the base end of a universal cord extending from an operation unit. Then, the simplicity of operation of the endoscopes can be improved by the above arrangements.

However, when a surgeon intends to execute medical treatment of a target portion, collection of a biopsy for the judgment of treatment, and like by introducing a treatment tool into a body cavity through a treatment tool channel formed in these endoscopes, it is difficult for the surgeon to freely operate the treatment tool with the left hand because the surgeon operates the curving knob of the operation unit with the left hand and displays a target portion on the screen of a monitor by operating an inserting portion gripped with the right hand. Accordingly, while surgeons have operated a treatment tool by obtaining cooperation from another doctors, nurses, and the like, it is difficult for the surgeons to communicate with them. As a result, there have been many requests from surgeons that they want to freely operate a treatment tool according to the judgment of themselves.

OBJECT OF THE INVENTION

An object of the present invention, which was made in view of the above circumstances, is to provide an endoscope device which improves the operability of a surgeon by improving not only curving operability but also the inserting property of an inserting portion and the operability of a treatment tool.

SUMMARY

An endoscope device of the present invention includes an inserting portion having a curving, portion, electric motors for generating driving forces for curving the curving portion, an operation unit for controlling the drive of the electric motors, a universal cord the base end of which is connected to an endoscope external unit, a coupling member with which the respective one ends of the inserting portion and the universal cord are coupled and which has a treatment tool inserting port, a holding unit for holding the coupling member, and a holding member for disposing the holding unit at a predetermined position of an operation bed.

An endoscope device of the present invention includes an inserting portion having a curving portion, electric motors for generating driving forces for curving the curving portion, an operation unit for controlling the drive the electric motors; a universal cord the base end of which is connected to an endoscope external unit, a coupling member with which the respective one ends of the inserting portion and the universal cord are coupled and which has a treatment tool inserting port, a holding member including a holding unit for holding the coupling member and disposing the holding unit at a predetermined position of an operation bed, wherein the holding unit includes a mechanism having a degree of freedom with respect to the inclining direction of the inserting portion or a mechanism having a degree of freedom with respect to the twist rotation of the inserting portion as well as the center position of the treatment tool inserting port of the coupling member is in approximate agreement with the center of twist rotation of the inserting portion.

According to this arrangement, since the operation unit is mounted at a desired position of, for example, the inserting portion, a surgeon can operate the operation unit while gripping the inserting portion with one hand and can operate a treatment tool with the other hand.

BRIEF DESCRIPTION OF THE DRAWINGS

FIG. 1 to FIG. 9 are views explaining a first embodiment of the present invention.

FIG. 1 is a view explaining an endoscope device having an endoscope of the present invention.

FIG. 5 is a view explaining a controlled state of a curving portion controlled by the operation unit.

FIG. 9 is a view explaining an example of arrangement of a motor unit coupled with an endoscope connector.

FIG. 10 to FIG. 17 are views explaining a second embodiment of the present invention.

FIG. 10 is a view explaining an endoscope device having a motor unit connected to the holding member of an endoscope main body.

FIG. 14 is a view explaining an example of connection of the motor unit to the holding member.

FIG. 17 is a view explaining another example of arrangement of the holding unit.

DETAILED DESCRIPTION OF PREFERRED EMBODIMENTS

Embodiments of the present invention will be described below with reference to the drawings.

First, a first embodiment will be described.

Figure 1:
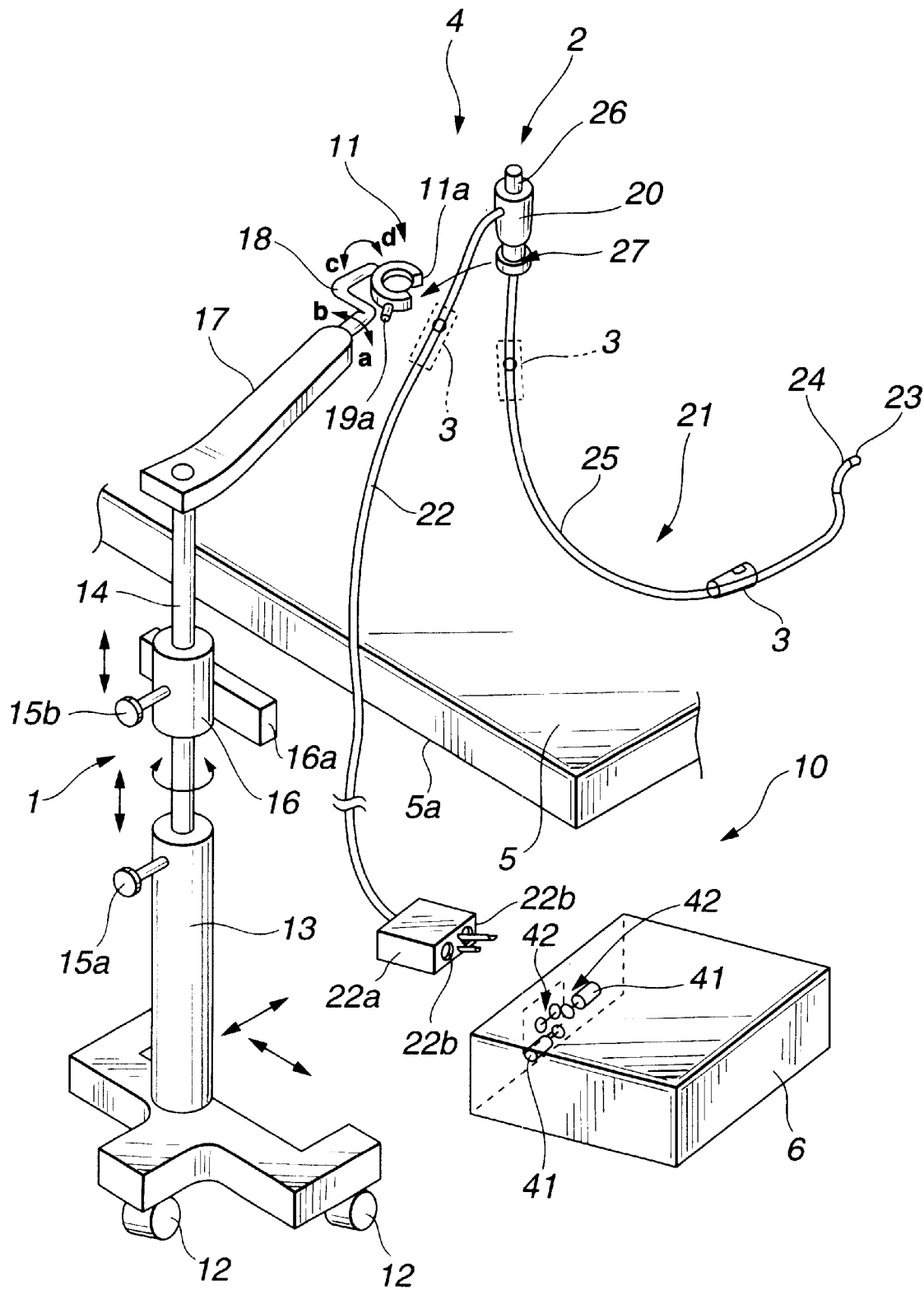
Figure 7A:
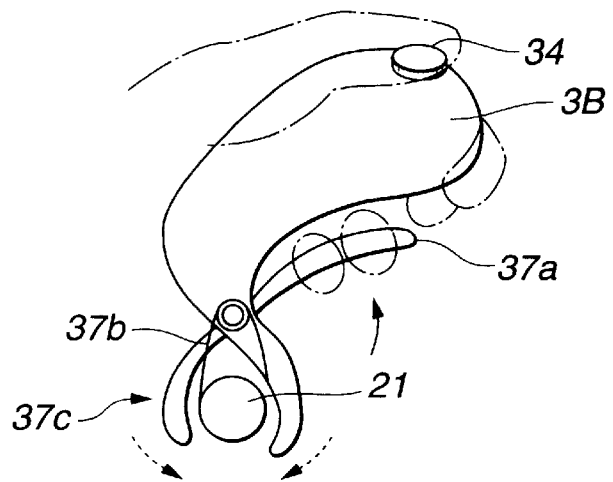
FIG. 7A is a view explaining still another arrangement of the operation unit.
Figure 7B:
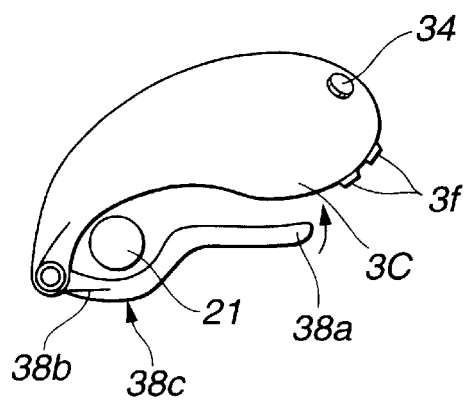
FIG. 7B is a view explaining a further arrangement of the operation unit.
Figure 7C:
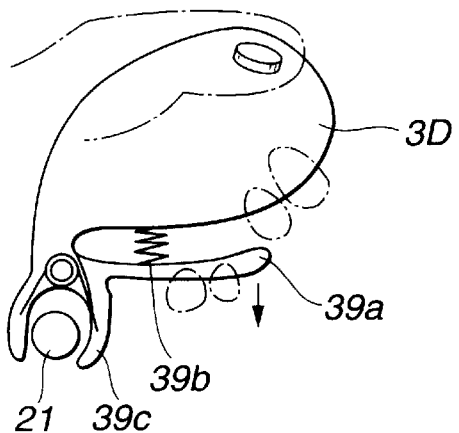
FIG. 7C is a view explaining a still further arrangement of the operation unit.
Figure 8A:
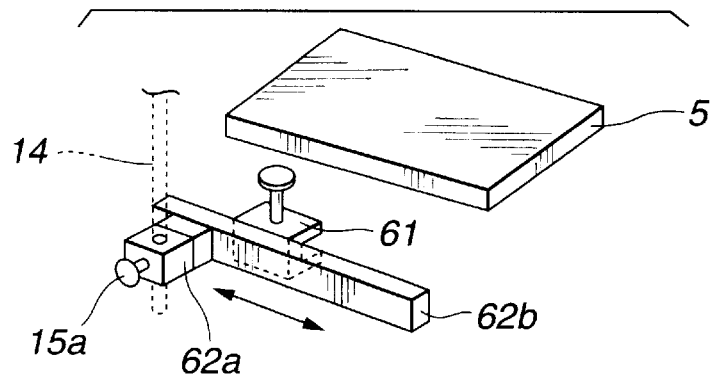
FIG. 8A is a view explaining another arrangement of a holding member.
Figure 8B:
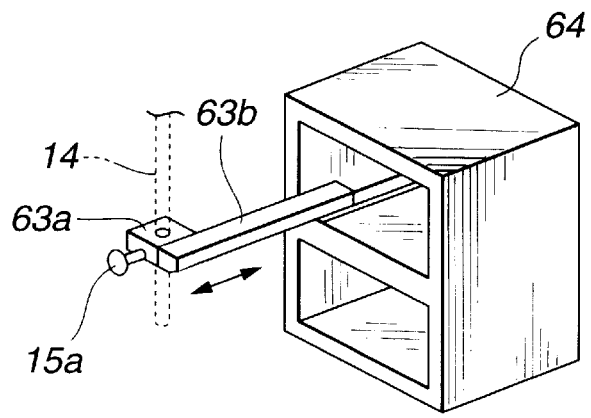
FIG. 8B is a view explaining still another arrangement of the holding member.
Figure 9:
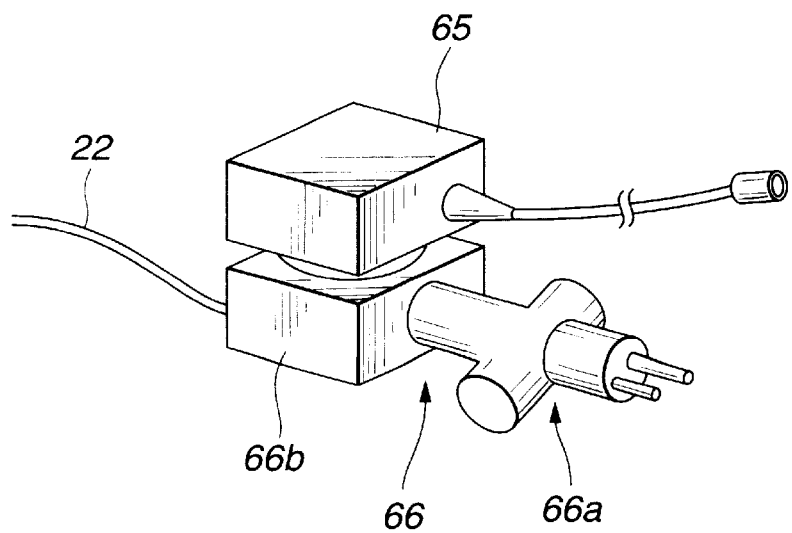

FIG. 1 to FIG. 9 are views explaining a first embodiment of the present invention. FIG. 1 is a view explaining an endoscope device having an endoscope of the present invention. FIG. 2A and FIG. 2B are views explaining the relationship of disposed position of a treatment tool insertion port disposed to a coupling member with respect to an operation bed. FIG. 3A and FIG. 3B are views explaining the arrangement and operation of a holding unit. FIG. 4A and FIG. 4B are views explaining an example of arrangement of an operation unit mounted on an inserting portion. FIG. 5 is a view explaining the controlled state of a curving portion controlled by the operation unit. FIG. 6A, FIG. 6B, and 6C are views explaining other examples of arrangement of the operation unit mounted on the inserting portion. FIG. 7A, FIG. 7B, and FIG. 6C are views explaining other examples of arrangement of the operation unit mounted on the inserting portion. FIG. 8A and FIG. 8B are views explaining other arrangements of holding member. FIG. 9 is a view explaining a n example of arrangement of a motor unit coupled with an endoscope connector.

Figure 2A:
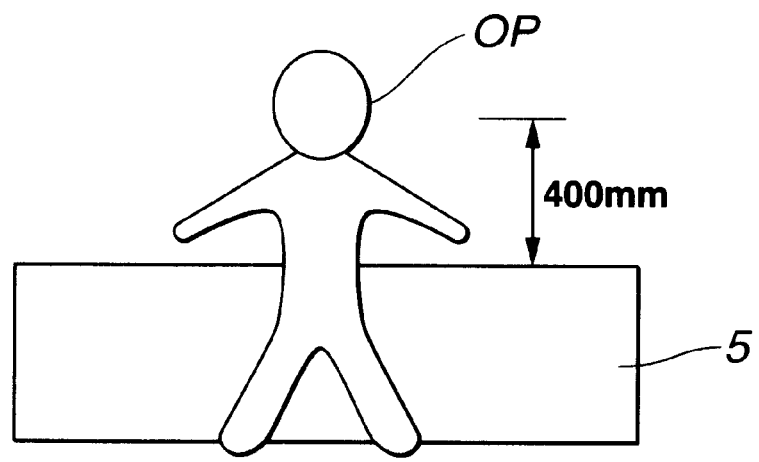
FIG. 2A is a view explaining the height range of a treatment tool insertion port from a bed surface.
Figure 2B:
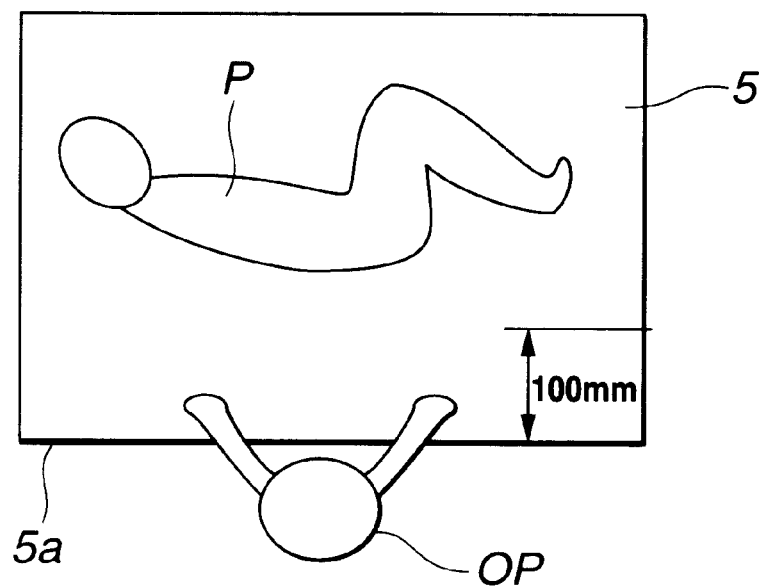
FIG. 2B is a view explaining the patient's side range of the treatment tool insertion port from a bed longitudinal side.
Figure 3A:
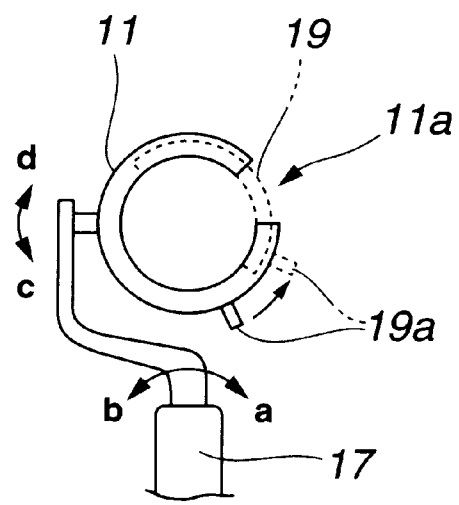
FIG. 3A is a view explaining an arrangement of a holding unit.
Figure 3B:
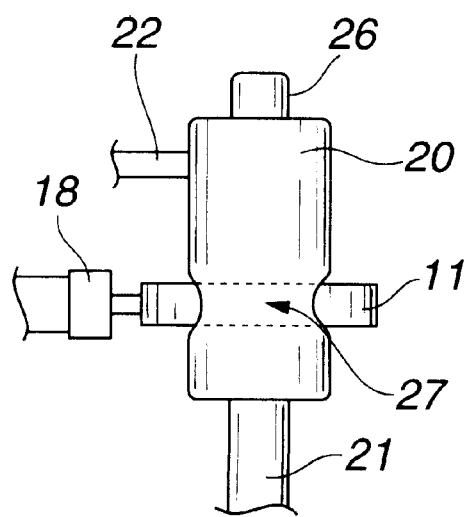
FIG. 3B is a view showing a state in which a coupling member is mounted on the holding unit.
Figure 4A:
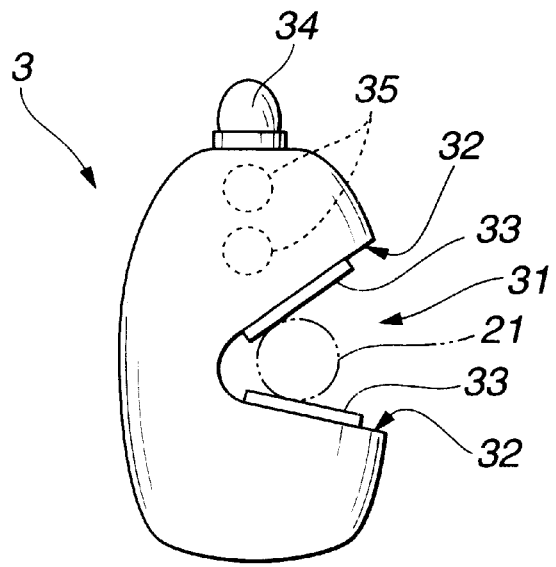
FIG. 4A is a view explaining the operation unit mounted on the inserting portion.
Figure 4B:
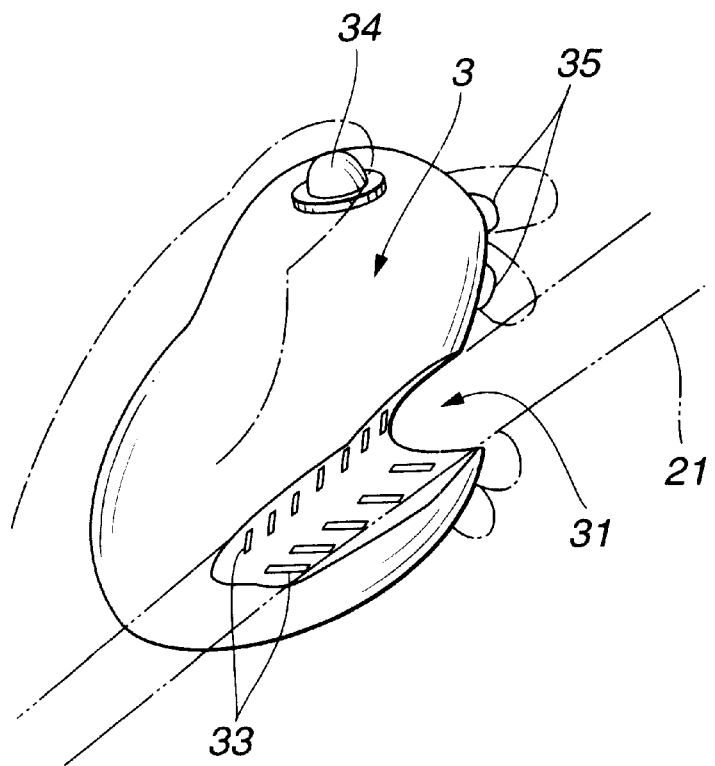
FIG. 4B is a view explaining a state in which the operation unit mounted on the inserting portion is operated.
Figure 6A:
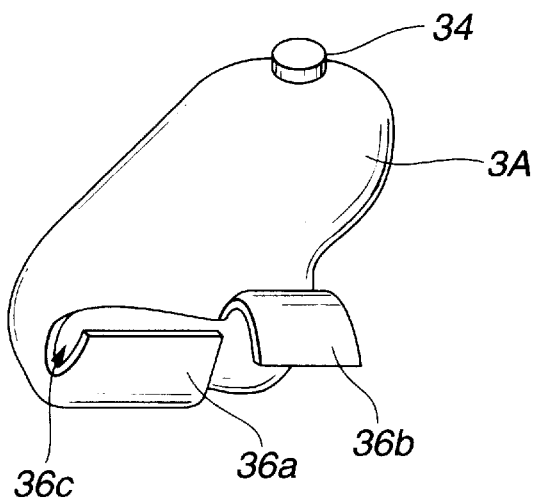
FIG. 6A is a view explaining another arrangement of the operation unit.
Figure 6B:
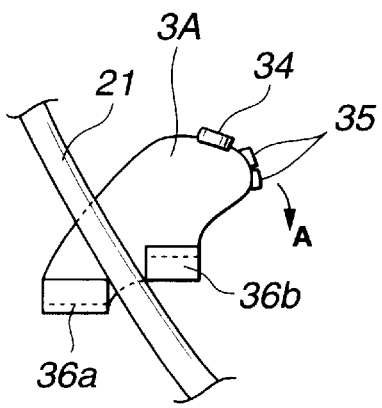
FIG. 6B is a view explaining a procedure for fixing the operation unit to the inserting portion integrally therewith.
Figure 6C:
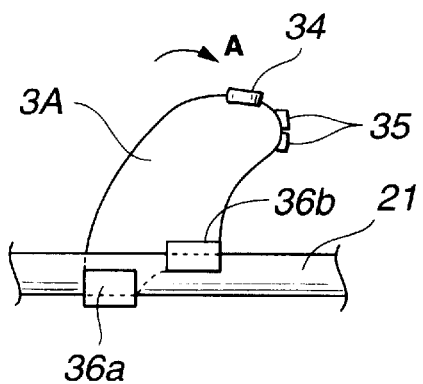
FIG. 6C is a view showing an integrally fixed state of the inserting portion and the operation unit.

Note that FIG. 2A is a view explaining the height range of the treatment tool insertion port from a bed surface. FIG. 2B is a view explaining the patient's side range of the treatment tool insertion port from a bed longitudinal side, and FIG. 3A is a view explaining the arrangement of the holding unit. FIG. 3B is a view showing a state in which the coupling member is mounted on the holding unit. FIG. 4A is a view explaining the operation unit mounted on the inserting portion. FIG. 4B is a view explaining a state in which the operation unit mounted on the inserting portion is operated. FIG. 6A is a view explaining another arrangement of the operation unit. FIG. 6B is a view explaining a procedure for fixing the operation unit to the inserting portion integrally therewith. FIG. 6C is a view showing an integrally fixed state of the inserting portion and the operation unit. FIG. 7A is a view explaining still another arrangement of the operation unit. FIG. 7B is a view explaining a further arrangement of the holding unit. FIG. 7C is a view explaining a still further arrangement of the operation unit. FIG. 8A is a view explaining another arrangement of the holding member. FIG. 8B is a view explaining still another arrangement of the holding member.

As shown in FIG. 1, an endoscope device 10 of this embodiment is composed of a holding member 1, an endoscope 4, and an endoscope unit 6. The holding member 1 is arranged such that it can dispose an approximately C-shaped holding unit 11 at a predetermined position of an operation bed 5. The endoscope 4 includes an endoscope main body 2 and an operation unit 3. The endoscope main body 2 includes a slender inserting portion 21, which is disposed by being attached to the holding unit 11, and a coupling member 20 with which a universal cord 22 is coupled. The operation unit 3 has such an arrangement that it can be detachably mounted on the inserting portion 21 or the universal cord 22 at a desired position. The endoscope unit 6 is an endoscope external unit, to which an endoscope connector 22*a* disposed to an end of the universal cord 22 of the endoscope main body 2 can be detachably fitted. The endoscope unit 6 houses, for example, a not shown light source unit, a not shown camera control unit, electric motors 41 arranged as, for example, one set for curving a curving portion to be described later in an up and down direction and a right and left direction, respectively, and the like.

Gear trains 42 each composed of, for example, a plurality of gears for transmitting the rotational driving force of the respective electric motors 41 are disposed in the endoscope unit 6. Connection between the gear trains 42 and the connection gears 22*b* disposed in the endoscope connector 22*a* causes a curving wire to be described later inserted into the universal cord 22 and the inserting portion 21 to be pulled and loosened.

Continuously disposed to the inserting portion 21 of the endoscope main body 2 from an extreme end sequentially in the following order are a hard extreme end portion 23, in which an observation optical system, an illumination optical system, and the like are disposed, the curving portion 24, in which a plurality of curving pieces to be described later, and the like are continuously connected to each other so as to permit the curving portion 24 to freely curve in, for example, up, down, right and right directions, and a soft and flexible tube portion 25. Then, the coupling member 20 is coupled with and fixed to the base end of the soft tube portion 25. The universal cord 22 is coupled with the coupling member 20 so that it has an intersecting angle of 90° with respect to the soft tube portion 25 coupled with the coupling member 20. With this arrangement, unsatisfactory operability which is caused by a loop formed when a twist operation is executed to the inserting portion 21 can be removed. As shown in FIG. 1, the intersecting angle between the inserting portion 21 coupled with the coupling member 20 and the universal cord 22 is 90°, and the position, where the coupling member 20 is held by the holding unit 11, is located nearer to the coupling portion side of an inserting portion than the coupling portion of a universal cord.

The coupling member 20 has a treatment tool insertion port 26 communicating with a treatment tool insertion channel (not shown) formed in the inserting portion 21. The treatment tool insertion port 26 is disposed so that its center is approximately in agreement with the center of rotation of the inserting portion 21 when it is twisted.

Note that reference numeral 27 denotes a fixing and holding portion which is to be disposed to the holding unit 11 and to which, for example, a concave shape is formed. The fixing and holding portion is formed nearer to the side where the soft tube portion 25 is coupled than the position where the universal cord 22 is coupled.

The holding member 1 is composed of the holding unit 11, a holding member main body 13, a support column 14, a first fixing screw 15*a*, a sliding member 16, a second fixing screw 15*b*, an arm member 17, and a crank member 18. The holding unit 11 includes a mechanism having a degree of freedom with respect to the inclining direction of the inserting portion 21 or a mechanism having a degree of freedom with respect to the twist rotation of the inserting portion 21. The coupling member 20 is detachably attached to the holding unit 11. The holding member main body 13 includes, for example, casters 12 which permit it to move front and back, and right and left. The support column 14 is composed of a round bar capable of changing its projecting length with respect to the holding member main body 13. The first fixing screw 15*a* fixes the length of the support column 14 projecting from the holding member main body 13 to a desired length state. The sliding member 16 is slidably disposed to the support column 14 and includes a guide portion 16*a* abutted against a longitudinal side portion 5*a* of the operation bed 5. The second fixing screw 15*b* fixes the guide portion 16*a* at a position having a desired height. The arm member 17 is fixed to the extreme end of the support column 14 and formed at a predetermined inclining angle with respect to the surface of the operation bed. The crank member 18 is arranged at an end of the arm member 17 so as to be free to move circulalry in the directions a and b of an arrow. Note that the holding unit 11 is arranged so as to be free to move circulalry in the directions c and d of an arrow with respect to the crank member 18. With this arrangement, when the inserting portion 21 is variously operated during an operation, even if the inclination of the coupling member 20 is changed by these operations, the crank member 18 and the holding unit 11 cope with the inclination of the coupling member 20 by moving circularly, respectively. The holding unit 11 can be adjusted so that the treatment tool insertion port can be disposed within a desired range above the surface of the operation bed and within a desired range from a longitudinal side end of the bed toward a patient side.

FIG. 2A and FIG. 2B are views explaining the relationship of disposed position of the insertion port of the treatment tool disposed to the coupling member with respect to the operation bed. Reference symbol OP denotes a surgeon and reference symbol P denotes a patient. The position where the holding unit 11 is disposed is adjusted with respect to the operation bed 5 by the surgeon. The surgeon turns the support column 14 with respect to the holding member main body 13, turns the arm member 17 with respect to the support column 14, or adjusts the projecting height of the arm member 17 in a state that the guide portion 16*a* of the sliding member 16 is abutted against the longitudinal side portion 5*a*. Accordingly, the position of the treatment tool insertion port 26, which is formed to the coupling member 20 to be disposed to the holding unit 11, is set within the range of, for example, 400 mm above the surface of the operation bed as shown in FIG. 2A, and within the range of, for example, 100 mm from the longitudinal side end of the bed toward the patient P side as shown in FIG. 2B. Note that, as described above, the holding member 1 can be moved to and set at any optional position with respect to the operation bed.

As shown in FIG. 3A, an opening 11*a*, through which the fixing and holding portion 27 passes, is formed to the holding unit 11 as well as the holding unit 11 includes a slide member 19 shown by a broken line and movably disposed so as to close the opening lla. The slide member 19 can be moved as shown by an arrow by operating a knob 19*a*. Accordingly, the coupling member 20 disposed to the holding unit 11 can be prevented from being removed therefrom by operating the knob 19*a* and closing the opening 11*a* with the slide member 19 as shown in FIG. 3B. At this time, the coupling member 20 is free to move circularly because it is loosely fitted into holding unit 11 so that the coupling member 20 can cope with the twist operation of the inserting portion 21.

As shown in FIG. 4A, the operation unit 3 has a cross sectional shape formed in, for example, an approximately ellipse shape, and the shape of the outer surface thereof is formed in consideration of a gripping property. A fixing groove 31, which is disposed to the inserting portion 21 or the universal cord 22 and formed in, for example, an approximately V-shape, is formed to a side of the operation unit 3. A plurality of projections 33 are disposed to the fixing surface 32 of the fixing groove 31 to stably hold and fix the operation unit 3 to the inserting portion 21 or to the universal cord 22.

Further, an operation convex portion 34, which can be, for example, tilted, is disposed to an upper side in the figure to operate the curving portion 24 up and down, and right and left. In FIG. 4B, various operation switches 35 are disposed at the extreme end 23 side of the inserting portion 21 located on a right side.

When the operation unit 3 is held and fixed at a desired position of, for example, the inserting portion 21, the surgeon can operate the operation unit 3 and the inserting portion 21 while gripping the operation unit 3 with the left hand as shown, for example, in FIG. 4B. That is, the surgeon can twist the inserting portion 21 by executing a twisting operation to the operation unit 3, can operate the curving portion by operating the operation convex portion 34 with the thumb, and further can operate the operation switches 35 with the first finger, or with the first finger and the second finger, and the like. Note that it is not limited to the left hand which operates the operation unit 3, and the operation unit 3 may be gripped with the right hand and the convex operating portion 34 and the operation switches 35 may be operated with fingers of the right hand.

As shown in FIG. 5, when, for example, the surgeon desires to curve the curving portion 24, for example, upward, he or she inclines the convex operating portion 34 of the operation unit 3 disposed to the inserting portion 21 to the extreme end 23 side. Thus, a curving operation indication signal corresponding to an inclining angle of the convex operating portion 34 is outputted from the operation unit 3 to an indicated value detector 51 disposed in, for example, the endoscope unit 6.

The indicated value detector 51 having received the curving operation instruction signal creates a motor drive signal for driving the electric motors 41 to curve the curving portion 24 in correspondence to the curving operation indicating signal and outputs the signal to a controller 52. The controller 52 having received the motor drive signal drives an up/down electric motor 41 in correspondence to the curving operation indicating signal through a motor controller 53 and a motor amplifier 54 which correspond to the motor drive signal.

Thus, the rotational driving force of the electric motor 41 is transmitted through the gear train 42 and the connection gear 22b to a pulley 22c which is rotated by the rotation of the connection gear 22b. A curving wire 55 has a base portion, which is fixed to the pulley 22c, and an extreme end fixed to a first curving piece 24f which is located at the front extremity of a plurality of curving pieces 24a constituting the curving portion 24. Therefore, the wire 55 is pulled and loosened by the rotation of the pulley 22c so that the curving portion 24 is curved upward.

Note that the curving operation indicating signal is transmitted from the operation unit 3 to the indicated value detector 51 by radio or wire. Further, reference numeral 56 denotes an encoder for detecting the number of rotation of the electric motor 41. Reference numeral 57 denotes a curving state detector for detecting the curving state of the curving portion 24 based on the number of rotation detected by the encoder 56. Reference numeral 58 denotes a wire tube for covering the curving wire 55.

The operation of the endoscope 4 arranged as described above will be described.

First, the coupling member 20, which has the soft tube portion 25 of the inserting portion 21, of the endoscope main body 2 is held by the holding unit 11 of the holding member 1, and the endoscope connector 22a disposed at the end of the universal cord 22 is connected to a predetermined position of the endoscope unit 6 in a predetermined state.

Next, the holding member main body 13 is moved so that the guide portion 16a of the sliding member 16 mounted on the support column 14 of the holding member 1 is abutted against the longitudinal side portion 5a of the operation bed. The holding member main body 13 is moved along the longitudinal side portion 5a, the support column 14 is turned, the arm member 17 is turned with respect to the support column 14, or the projecting length of the support column 14 is adjusted so that the treatment tool insertion port 26 of the coupling member 20 is located at a predetermined position.

Then, after the treatment tool insertion port 26 of the coupling member 20 has been disposed at a position desired by the surgeon, he or she attaches the operation unit 3 to a desired position (for example, the position shown by the solid line in FIG. 1).

Next, the surgeon grips the operation unit 3 and the inserting portion 21 with one hand and inserts the extreme end 23 into, for example, the anus, inserts the extreme end 23 to the vicinity of a target portion by suitably operating the convex operating portion 34 disposed to the operation unit 3 or by twisting the inserting portion 21, and displays the image of the target portion on the screen of a monitor (not shown).

Here, a treatment tool is inserted toward a body cavity from treatment tool insertion port 26, when necessary. The operation of the treatment tool at this time is carried out with the hand which grips neither the operation unit 3 nor the inserting portion 21, that is, with the other unoccupied hand.

As described above, the surgeon can execute various operations such as a curving operation as well as a twisting operation, an advancing/retracting operation, and the like of the inserting portion 21 only with the one hand gripping the operation unit 3 in such a manner that the coupling member 20 constituting the endoscope main body 2 is held by the holding unit 11 of the holding member 1 and the operation unit 3 is attached to a desired position of the inserting portion 21 or the universal cord 22 which constitute the endoscope main body 2.

With this operation, the surgeon can freely operate the treatment tool with the other hand without the need of getting the cooperation of other doctors and nurses in order to have them execute the operation and the like of the treatment tool. Further, since the surgeon can insert the inserting portion 21 to the target portion with the one hand, when the inserting portion 21 is inserted from, for example, the anus, the surgeon can execute jobs such as changing of an inserting direction, releasing of a pressed state, and the like as he or she desires by pressing a portion where it is supposed that the extreme end 23 is located with the other unoccupied hand.

Further, since the center of the treatment tool insertion port 26 formed to the coupling member 20 is caused to be in approximate agreement with the center of twist rotation of the inserting portion 21, the insertion of the treatment tool into the inserting portion 21 and various operations can be smoothly carried out regardless of a twisted state of the inserting portion.

Further, the crank member 18 is disposed to the arm member 17 so as to be free to move circularly with respect to a predetermined direction as well as the holding unit 11 is disposed to the crank member 18 so as to be free to move circularly with respect to a predetermined direction. Thus, when the inserting portion 21 is to be inserted to a target portion, the crank member 18 and the holding unit 11 move circularly with respect to the arm member 17 and the crank member 18, respectively in accordance with a change of inclination of the inserting portion 21, which permits the surgeon to stably execute an inserting operation.

Note that when the operation unit 3 is washed and sterilized after it is used, it is arranged to have a water tight structure. In contrast, when the operation unit 3 has such a structure that it is not washed and sterilized after it is used, the operation unit 3 is covered with a cover member or the like in use, and the cover member discarded after it is used.

Further, while this embodiment shows the arrangement in which the operation unit 3 is held and fixed by, for example, the inserting portion 21, fixing of the operation unit 3 to the inserting portion 21 or the like is not limited to such an arrangement that it is held and fixed by the fixing groove 31. For example, as shown in FIG. 6A, an operation unit 3A having a fixing groove 36c formed of a first return portion 36a and a second return portion 36b may be employed.

When the fixing groove 36c is composed of the first return portion 36a and the second return portion 36b, the inserting portion 21 is disposed obliquely to the gap between the first return portion 36a and the second return portion 36b as shown in FIG. 6B, and, for example, the operation unit 3A is inclined as shown by an arrow, it can be fixed at a desired position of the inserting portion 21 as shown in FIG. 6C.

As other arrangement, there may be employed such a type that an operation unit 3B is disposed to the inserting portion 21 in such a manner that, for example, a lever 37a is disposed as shown in FIG. 7A, and a clamp portion 37c is moved against the urging force of a spring 37b and tightened against the inserting portion 21 as shown by the arrows of broken lines by moving the lever 37a in the direction shown by the arrow of a solid line. Further, as shown in FIG. 7B, there may be employed such a type that the inserting portion 21 is disposed to a clamp portion 38c, which is tightened by moving a lever 38a in the direction of an arrow against the urging force of a spring 38b so as to dispose the inserting portion 21 to an operation unit 3C. Furthermore, as shown in FIG. 7C, there may be employed such a type that the operation unit 3B is disposed to the inserting portion 21 by tightening the inserting portion 21 by a clamp portion 39c by moving a lever 39a with the urging force of a spring 39b in the direction of an arrow.

Further, in the aforementioned embodiment, while the casters 12 are disposed to the holding member main body 13 so that the holding member 1 can be free to move, an arrangement shown in, for example, FIG. 8A may be employed. That is, a column holding unit 62a, which can freely adjust the projecting height of the support column 14, is disposed to a slide member 62b capable of sliding in the direction of an arrow, and the slide member 62b is attached to the longitudinal side portion 5a of the operation bed 5 by means of a fixing member 61 so as to be movable in the longitudinal direction of the bed. Further, as shown in FIG. 8B, a slide member 63b capable of expanding and contracting in the direction of an arrow may be disposed to a cart 64, which is free to move and on which an endoscope external unit is mounted, and a column holding unit 63a capable of freely adjusting the projecting height of the support column 14 may be disposed to the slide member 63b.

Furthermore, this embodiment shows the arrangement in which the electric motors 41 are disposed in the endoscope unit 6. However, the electric motors 41 may be arranged as a motor unit, and further an endoscope connector 66 may be composed of a light source connector 66a and a driving force transmission connector 66b. In this case, as shown in FIG. 9, the motor unit 65 may be connected to the driving force transmission connector 66b of the endoscope connector 66, and further an end of the universal cord 22 may be connected to the driving connector 66b.

Next, a second embodiment will be described.

Figure 10:
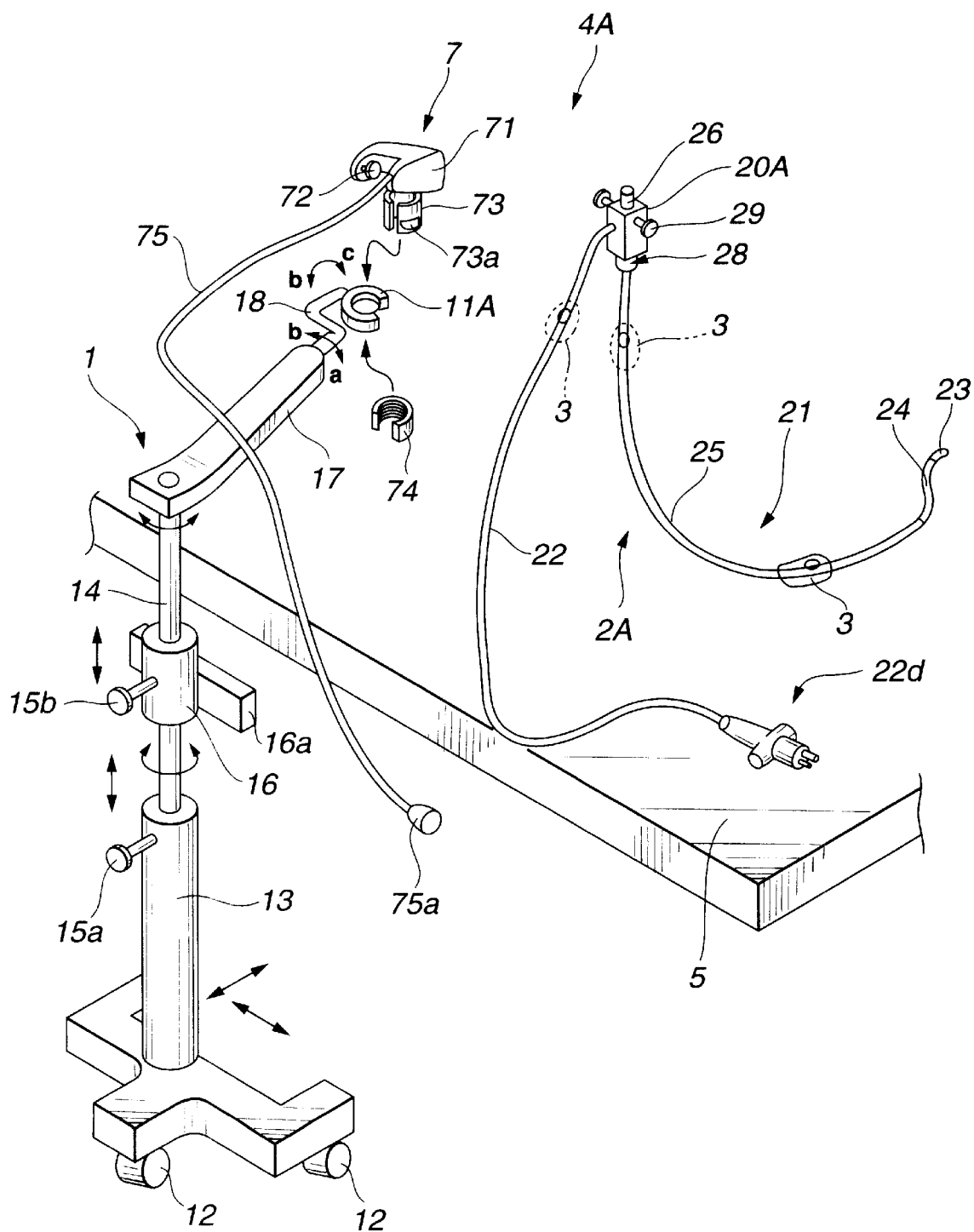
Figure 13A:
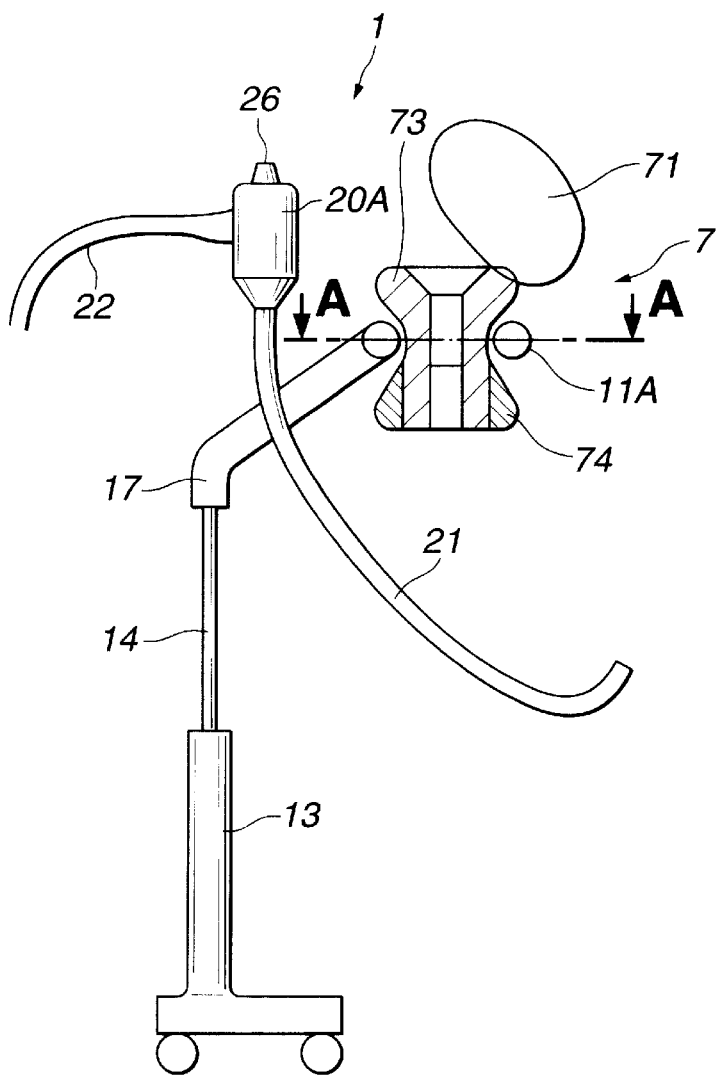
FIG. 13A is a view showing the holding unit on which the motor unit is mounted and an endoscope main body.
Figure 13B:
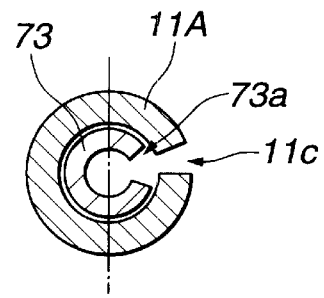
FIG. 13B is a sectional view showing the A—A cross section of FIG. 13A.
Figure 14:
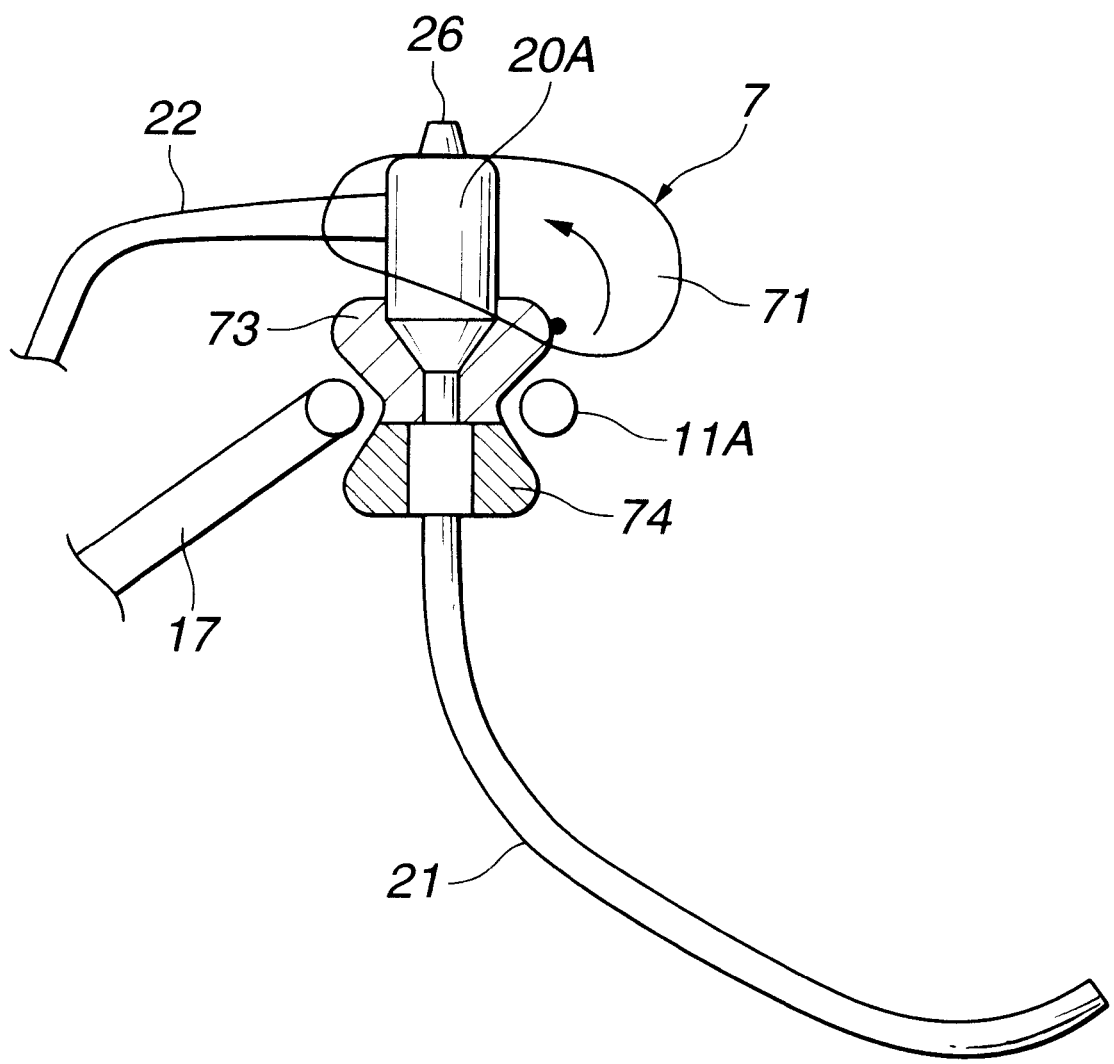
Figure 16A:
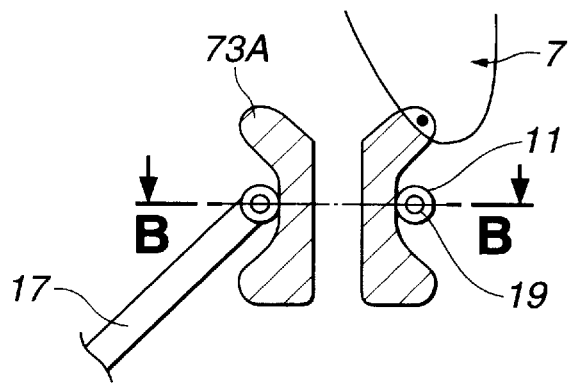
FIG. 16A is a sectional view explaining the arrangement of the holding unit.
Figure 16B:
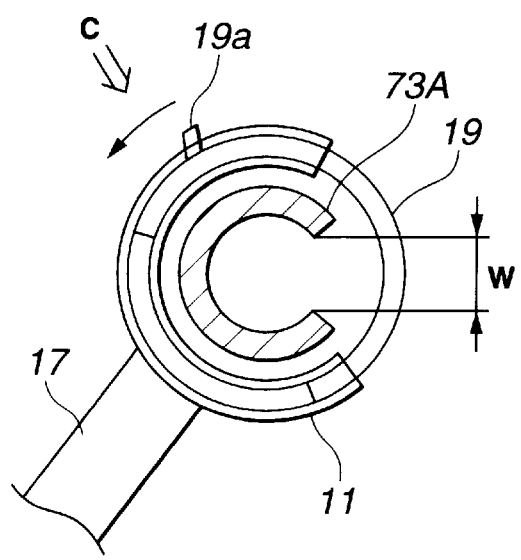
FIG. 16B is a sectional view showing the B—B cross section of FIG. 16A.
Figure 16C:
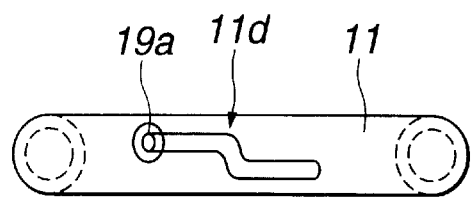
FIG. 16C is a view when viewed from the arrow C side of FIG. 16B.
Figure 17:
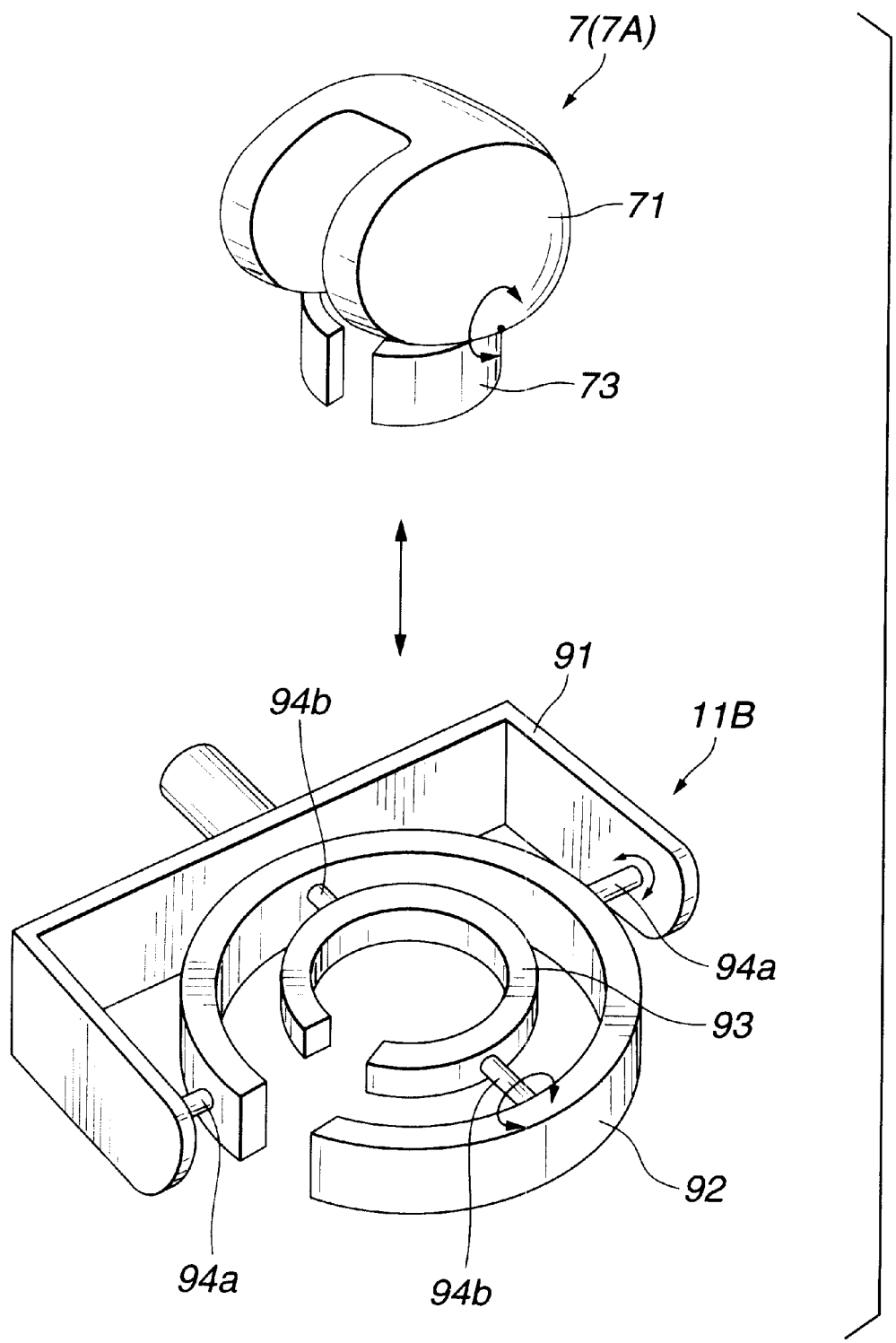

FIG. 10 to FIG. 17 are views explaining the second embodiment of the present invention. FIG. 10 is a view explaining an endoscope device having a motor unit connected to the holding member of an endoscope main body. FIG. 11 is a view explaining the holding member and the motor unit. FIG. 12 is a view explaining a mounting/dismounting mechanism for the holding member and the motor unit. FIG. 13 is a view explaining a state in which an endoscope main body is mounted on the holding unit on which the motor unit is mounted. FIG. 14 is a view explaining an example of connection of the motor unit to the holding member. FIG. 15 is a view explaining another example of connection of the motor unit to the holding member. FIG. 16 is a view explaining another example of arrangement of the holding unit. FIG. 17 is a view explaining still another example of arrangement of the holding unit.

Figure 11A:
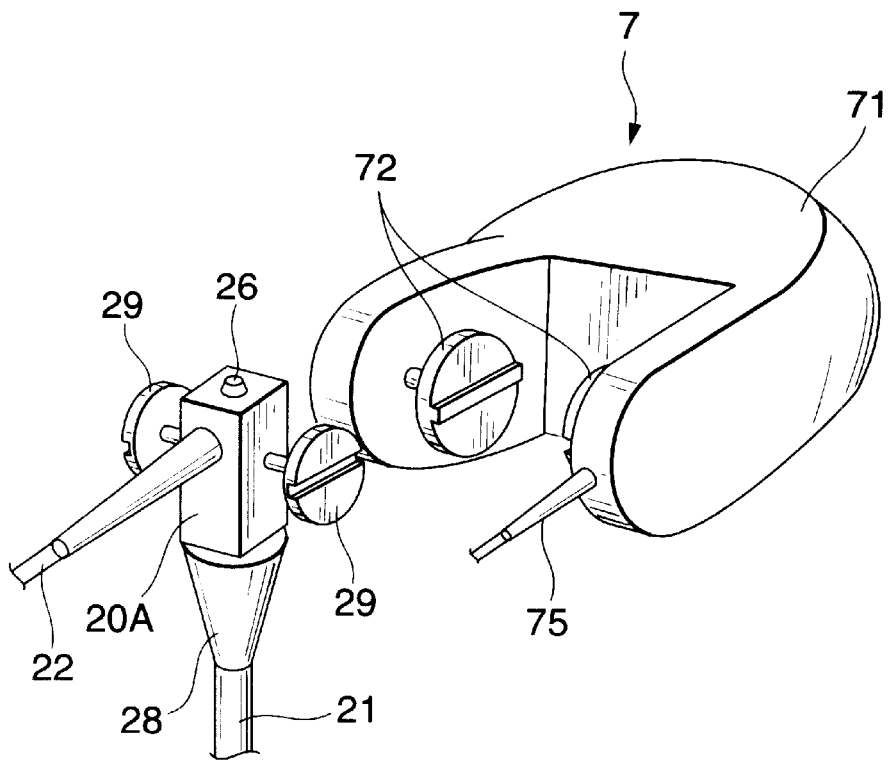
FIG. 11A is a perspective view showing the holding member and the motor unit.
Figures 11B, 11C:
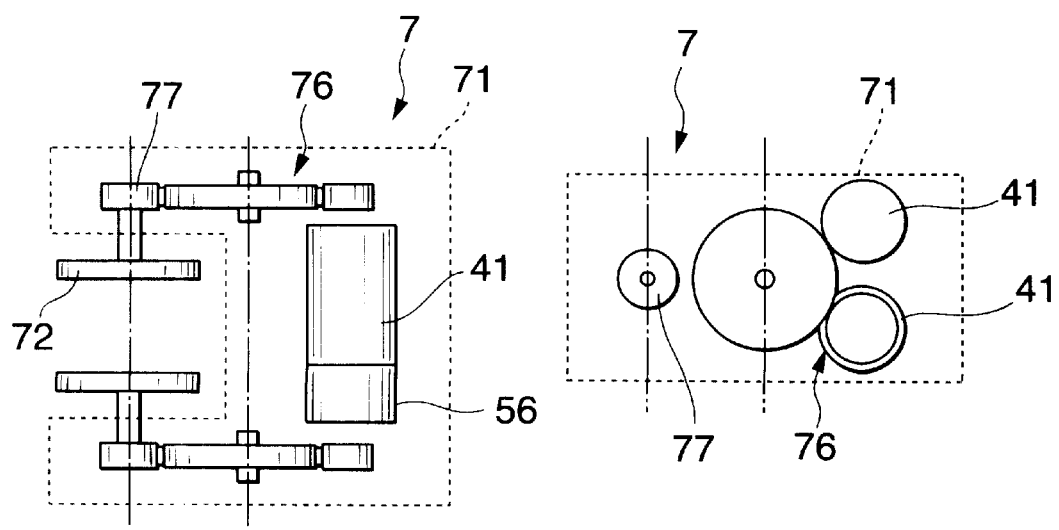
FIG. 11B is a plan view explaining the internal arrangement of a unit main body.
FIG. 11C is a side elevational view explaining the internal arrangement of the unit main body.
Figure 12A:
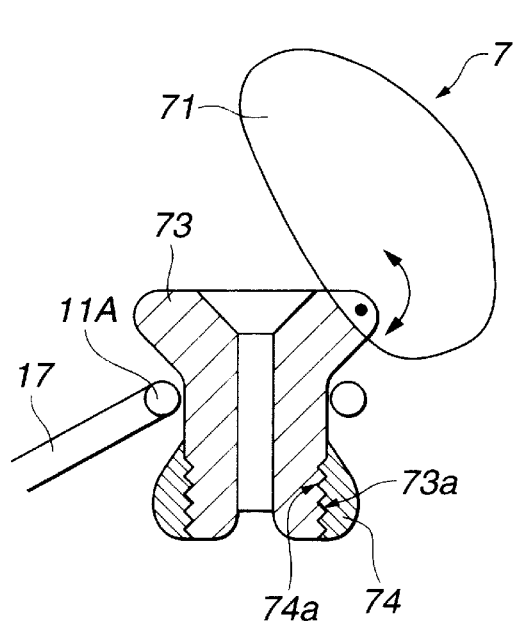
FIG. 12A is a view explaining a state in which the motor unit is mounted on a holding unit.
Figure 12B:
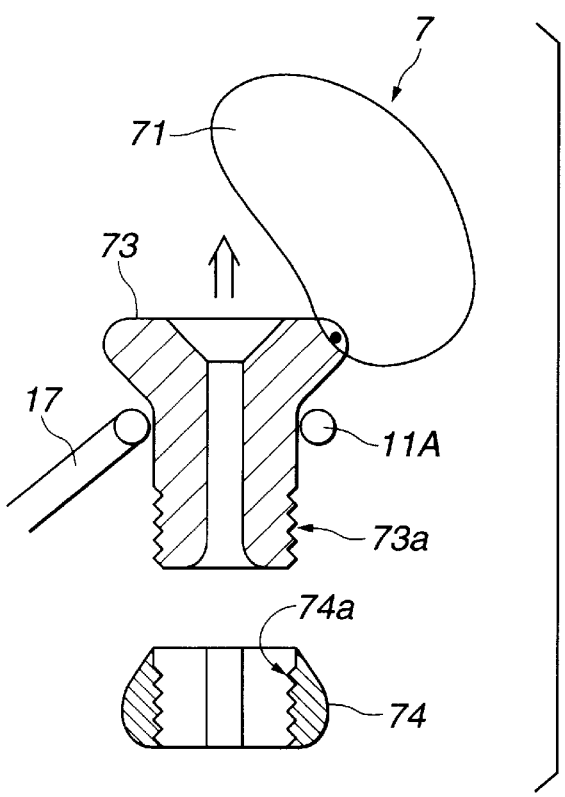
FIG. 12B is a view explaining a state in which the motor unit is removed from the holding unit.
Figure 15A:
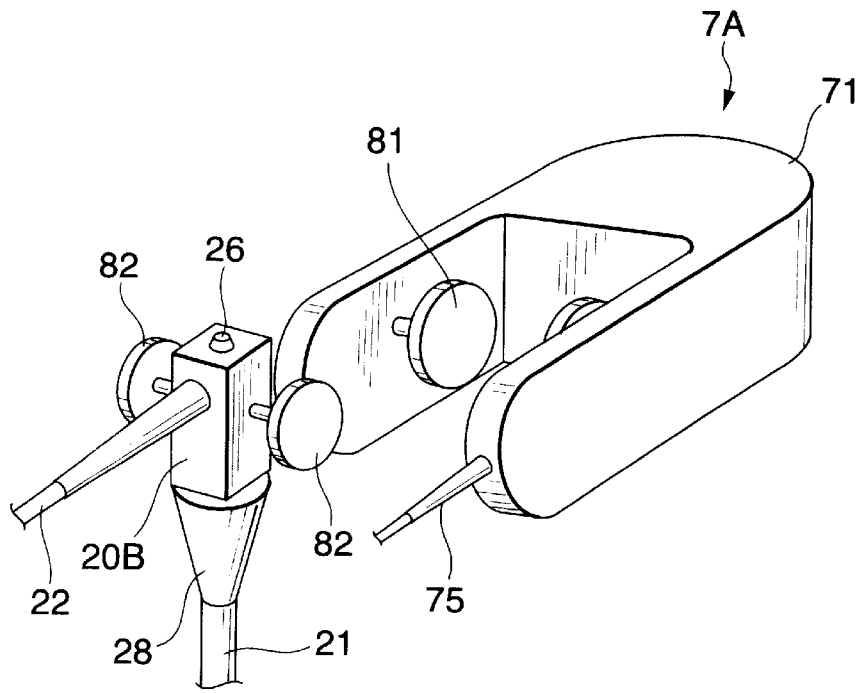
FIG. 15A is a perspective view showing the holding member and the motor unit.
Figure 15B:
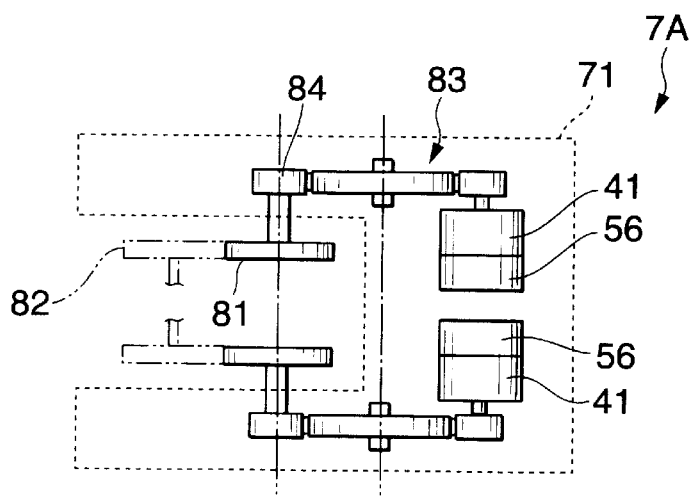
FIG. 15B is a plan view explaining the internal arrangement of the unit main body.
Figure 15C:
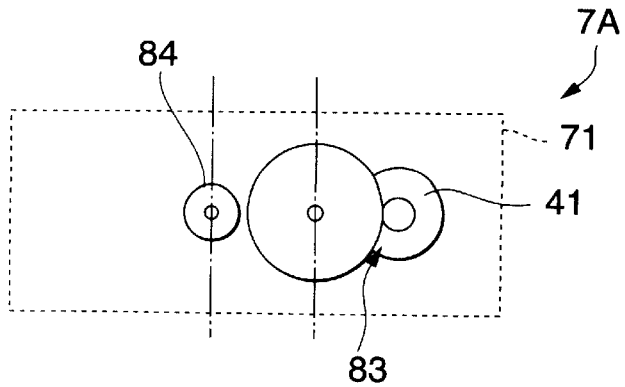
FIG. 15C is a side elevational view explaining the internal arrangement of the unit main body.

Note that FIG. 11A is a perspective view showing the holding member and the motor unit. FIG. 11B is a plan view explaining the internal arrangement of a unit main body. FIG. 11C is a side elevational view explaining the internal arrangement of the unit main body. FIG. 12A is a view explaining a state in which the motor unit is mounted on the holding unit. FIG. 12B is a view explaining a state in which the motor unit is removed from the holding unit. FIG. 13A is a view showing the holding unit on which the motor unit is mounted and the endoscope main body. FIG. 13B is a sectional view showing an A—A cross section of FIG. 13A. FIG. 15A is a perspective view showing the holding member and the motor unit. FIG. 15B is a plan view explaining the internal arrangement of the unit main body. FIG. 15C is a side elevational view explaining the internal arrangement of the unit main body. FIG. 16A is a sectional view explaining an arrangement of the holding unit. FIG. 16B is a sectional view showing a B—B cross section of FIG. 16A. FIG. 16C is a view when FIG. 16B is observed from an arrow C side.

As shown in FIG. 10, an endoscope 4A in this embodiment is arranged such that a motor unit 7 having electric motors for curving and driving a curving portion 24 can be attached to an approximately-C-shaped holding unit 11A constituting a holding member 1. The coupling member 20A of the endoscope main body 2A includes curving couplings 29, which are to be coupled with unit side couplings 72 disposed to the motor unit 7. The motor unit 7 is mainly composed of an approximately-U-shaped unit main body 71, a mounting portion 73 for disposing the unit main body 71 to the holding unit 11A, and an approximately-C-shaped fixture 74 for coupling and fixing the mounting portion 73 with and to the holding unit 11A. Note that the same arrangements as those of the first embodiment are denoted by the same reference numerals and the description thereof is omitted.

As shown in FIG. 11A to FIG. 11C, the two electric motors 41 are disposed in the unit main body 71 of the motor unit 7 in, for example, an upper and lower positional relationship to curve the curving portion 24 in an up and down direction and a right and left direction. The driving force of each of the respective electric motors 41 is transmitted to transmission gears 77 with which the unit side couplings 72 are provided integrally therewith through a corresponding gear train 76. Note that reference numeral 75 denotes a motor cable which extends in the same direction as the universal cord 22 and connected to a not shown controller including an indicated value detector, motor controllers, a power supply unit, and the like which are not shown through a connector 75a.

On the other hand, the coupling member 20A includes the curving couplings 29 which are to be inserted into and engaged with the unit side coupling 72. As shown in the figure, the motor unit 7 is disposed at a position confronting the coupling portion of the universal cord 22 attached to the coupling member 20A so that the weight of the holding unit 11A can be balanced.

Note that the curving coupling 29 includes a not shown pulley to which fixed is the other end of a curving wire one end of which is fixed to a first curving piece as shown in FIG. 5. Further, reference numeral 28 denotes a taper-shaped coupling and mounting portion 28 to be disposed to the holding unit 11A.

As shown in FIG. 12A, when the motor unit 7 is to be mounted on the holding unit 11A, the mounting portion 73 is disposed to the holding unit 11A, and the female screw portion 74a of the fixture 74 is screwed on the male screw portion 73a of the mounting portion 73 so as to arrange them integrally with each other. With this arrangement, the mounting portion 73 of the motor unit 7 is fitted to the holding unit 11A in a loose state.

In contrast, when the motor unit 7 is to be removed from the holding unit 11A, the screwed state of the male screw portion 73a of the mounting portion 73 and the female screw portion 74a of the fixture 74 which are arranged integrally with each other is released as shown in FIG. 12B. With this arrangement, the mounting portion 73 is moved from the holding unit 11A as shown by an arrow, which permits the motor unit 7 to be removed from the holding unit 11A. Note that the unit main body 71 of the motor unit 7 is mounted so as to move circularly with respect to the mounting portion 73 as shown by an arrow.

Next, a procedure for mounting the coupling member 20A ion the mounting portion 73 will be described.

As shown in FIG. 13B, a cutout portion 73a is formed to the mounting portion 73. As a result, when the coupling member 20A of the endoscope main body 2 is to be mounted on the holding unit 11A, first, the motor unit main body 71 is held in a state inclined with respect to the mounting portion 73, and the cutout portion 73a of the mounting portion 73 is caused to be in agreement with the opening portion 11c of the holding unit 11A as shown in FIG. 13A and FIG. 13B.

Next, the inserting portion 21 is caused to pass through the opening portion 11c and the cutout portion 73a so that the inserting portion 21 is inserted to and disposed at a predetermined position in the mounting portion 73. Then, thereafter, the coupling member 20A is disposed at a predetermined position of the mounting portion 73.

Subsequently, as shown in FIG. 14, the unit main body 71 is moved circularly to a predetermined position as shown by an arrow. With this operation, the curving couplings 29 of the coupling member 20A are in a state of engagement with the unit side couplings 72 of the motor unit 7, by which the mounting is completed.

Thereafter, as described in the above first embodiment, an operation unit 3 is mounted on a predetermined position, and observation, medical treatments, and the like are executed.

As described above, since the motor unit 7 is mounted on the holding unit 11A of the holding member 1, the responsiveness of an operation wire can be greatly improved by reducing the length of the operation wire corresponding to the universal cord, in addition to the advantage of the aforementioned first embodiment.

Note that the arrangement of the motor unit 7 is not limited to the arrangement shown in FIG. 11, and it may be arranged such that the driving forces of the two electric motors 41 disposed to the unit main body 71 may be transmitted to transmission gears 84 with which unit side gears 81 are arranged integrally with each other through corresponding gear trains 83 as shown in, for example, FIG. 15A to FIG. 15C. Note that reference numeral 82 denotes curving gears which are meshed with the unit side gears 81 disposed to the coupling member 20A. Note that each of the curving gears 82 includes a not shown pulley to which fixed is the other end of the curving wire one end of which is fixed to the first curving piece.

Further, as shown in FIG. 16A to FIG. 16C, the holding unit 11 having the slide member 19 shown in the first embodiment may be disposed to the arm member 17. With this arrangement, the inserting portion 21 can be reliably prevented from being removed from the holding unit 11. Note that reference numeral 11d denotes a knob groove in which the knob 19a moves.

Further, as shown in FIG. 17, a holding unit 11B may be arranged as a gimbal which is composed of a first swing member 92 and a second swing member 93, the first swing member 92 being movable circularly in the directions a and b of an arrow with respect to a first shaft portion 94a fixed to a fixing member 91 fixed to an end of the arm member 17, and the second swing member 93 being movable circularly in the directions c and d of an arrow with respect to a second shaft portion 94b fixed to the first swing member 92. With this arrangement, when the inserting portion 21 is operated in various directions during an operation, the first swing member 92 and the second swing member 93 move circularly, respectively in correspondence to the inclination of the coupling member 20.

The present invention is not limited to only the aforementioned embodiments and may be variously modified within the range which does not depart from the gist of the present invention.

As described above, according to the present invention, there can be provided an endoscope which improves the operability of a surgeon by improving not only a curving operability but also the insertion operability of an inserting portion and the operability of a treatment tool.

What is claimed is:

1. An endoscope device comprising:
   an inserting portion having a curving portion;
   electric motors for generating driving forces for curving the curving portion;
   an operation unit for controlling the drive of the electric motors;
   a universal cord the base end of which is connected to an endoscope external unit;
   a coupling member with which the respective one ends of the inserting portion and the universal cord are coupled and which has a treatment tool inserting port;
   a holding unit for holding the coupling member; and
   a holding member for disposing the holding unit at a predetermined position of an operation bed;
   wherein the electric motors are operatively connected to the coupling member and separable therefrom.

2. In claim 1, the operation unit is free to be mounted on and dismounted from the inserting portion or the universal cord at an optional position.

3. In claim 1, a motor unit includes the electric motors, and the motor unit can be mounted on the holding unit.

4. In claim 2, a motor unit includes the electric motors and the motor unit can be mounted on the holding unit.

5. In claim 3, the position where the motor unit is disposed is a position confronting the coupling portion of the universal cord attached to the coupling member.

6. In claim 3, motor cables extending from the motor unit extend in the same direction as the universal cord.

7. In claim 1, a center position of the treatment tool inserting port of the coupling member is in approximate agreement with the center of twist rotation of the inserting portion.

8. In claim 1, the holding unit includes a mechanism having a degree of freedom with respect to the inclining direction of the inserting portion or a mechanism having a degree of freedom with respect to the twist rotation of the inserting portion.

9. In claim 1, the holding unit can be adjusted so that the treatment tool insertion port is disposed within a desired range above the surface of an operation bed and within a desired range from a longitudinal side end of the bed toward a patient side.

10. In claim 1, the holding member can be moved to and set at any optional position with respect to an operation bed.

11. In claim 10, the holding member has a guide portion for making movement while maintaining a predetermined interval with respect to the operation bed.

12. In claim 1, the intersecting angle between the inserting portion coupled with the coupling member and the universal cord is 90°, and the position where the coupling member is held by the holding unit is located nearer the coupling portion side of the inserting portion than the coupling portion of the universal cord.

13. An endoscope device comprising:

an inserting portion having a curving portion;

electric motors for generating driving forces for curving the curving portion;

an operation unit for controlling the drive of the electric motors;

a universal cord the base end of which is connected to an endoscope external unit;

a coupling member with which the respective one ends of the inserting portion and the universal cord are coupled and which has a treatment tool inserting port; and a holding member including a holding unit for holding the coupling member and disposing the holding unit at a predetermined position of an operation bed, wherein the holding unit includes a mechanism having a degree of freedom with respect to the inclining direction of the inserting portion or a mechanism having a degree of freedom with respect to the twist rotation of the inserting portion as well as the center position of the treatment tool inserting port of the coupling member is in approximate agreement with the center of twist rotation of the inserting portion;

wherein the electric motors are operatively connected to the coupling member and separable therefrom.

* * * * *